United States Patent
O'Connor et al.

(10) Patent No.: US 8,122,888 B2
(45) Date of Patent: Feb. 28, 2012

(54) ARM POSITIONER FOR DIAGNOSTIC PROCEDURE

(76) Inventors: Anne C. O'Connor, Carlsbad, CA (US); Steven F. Bierman, Del Mar, CA (US); Douglas Bates, La Jolla, CA (US)

( * ) Notice: Subject to any disclaimer, the term of this patent is extended or adjusted under 35 U.S.C. 154(b) by 433 days.

(21) Appl. No.: 12/272,642

(22) Filed: Nov. 17, 2008

(65) Prior Publication Data
US 2009/0131780 A1    May 21, 2009

Related U.S. Application Data

(60) Provisional application No. 60/988,657, filed on Nov. 16, 2007.

(51) Int. Cl.
*A61G 15/00* (2006.01)
*A61F 5/00* (2006.01)

(52) U.S. Cl. .................................. 128/845; 602/21

(58) Field of Classification Search ............ 128/845, 128/846, 848, 878; 5/632, 637, 636, 646, 5/647; 602/21, 20, 5, 1
See application file for complete search history.

(56) References Cited

U.S. PATENT DOCUMENTS

| | | | | |
|---|---|---|---|---|
| 3,931,654 A * | 1/1976 | Spann | ................................ | 5/650 |
| 4,265,232 A * | 5/1981 | Stonich | ............................ | 5/647 |
| 5,046,487 A * | 9/1991 | Scott | ................................ | 601/27 |
| 5,060,638 A * | 10/1991 | Bodine, Jr. | ...................... | 602/21 |
| 5,323,786 A * | 6/1994 | Juhasz | ........................... | 128/845 |
| 5,485,856 A * | 1/1996 | Buckland | ........................... | 5/647 |
| 5,537,702 A * | 7/1996 | Brown-Milants et al. | ........ | 5/632 |
| 5,716,334 A * | 2/1998 | Wade | ................................ | 602/6 |
| 2009/0000625 A1 * | 1/2009 | Alfery | .......................... | 128/878 |

* cited by examiner

*Primary Examiner* — Patricia Bianco
*Assistant Examiner* — Tarla Patel
(74) *Attorney, Agent, or Firm* — Knobbe Martens Olson & Bear, LLP

(57) ABSTRACT

An arm positioning system for a diagnostic procedure such as an MRI can include a positioning block and a retention device (such as a thumb strap). The retention device and the positioning block can be coupled together (e.g. by hook and loop fasteners) to allow them to position a patient's arm in various desired positions. The retention device and positioning block can be composed of materials that do not interfere with the diagnostic device. The retention device and positioning block also can be configured to accommodate left and right arms and variation among arm, hand, and digit sizes of patients.

26 Claims, 8 Drawing Sheets

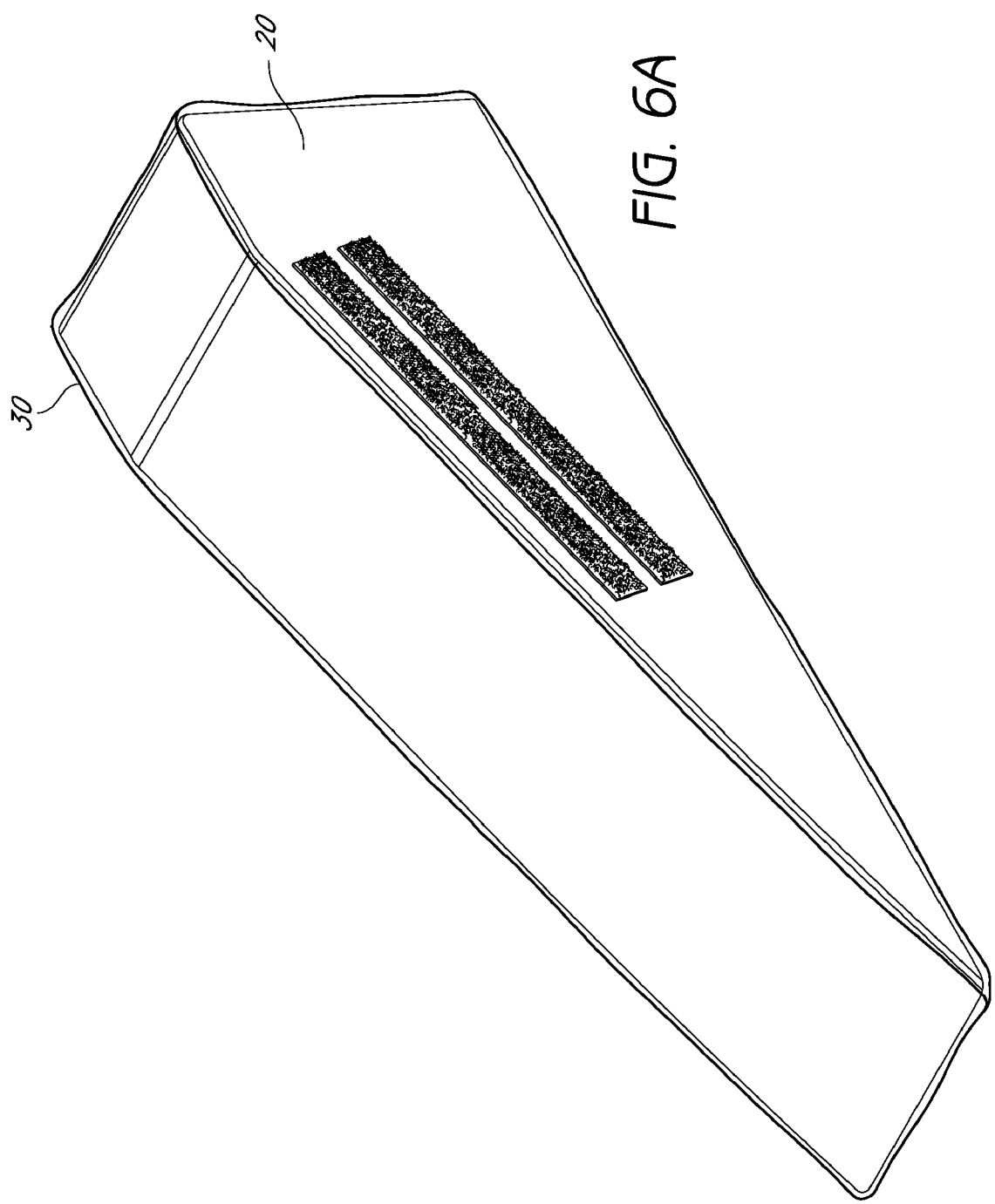

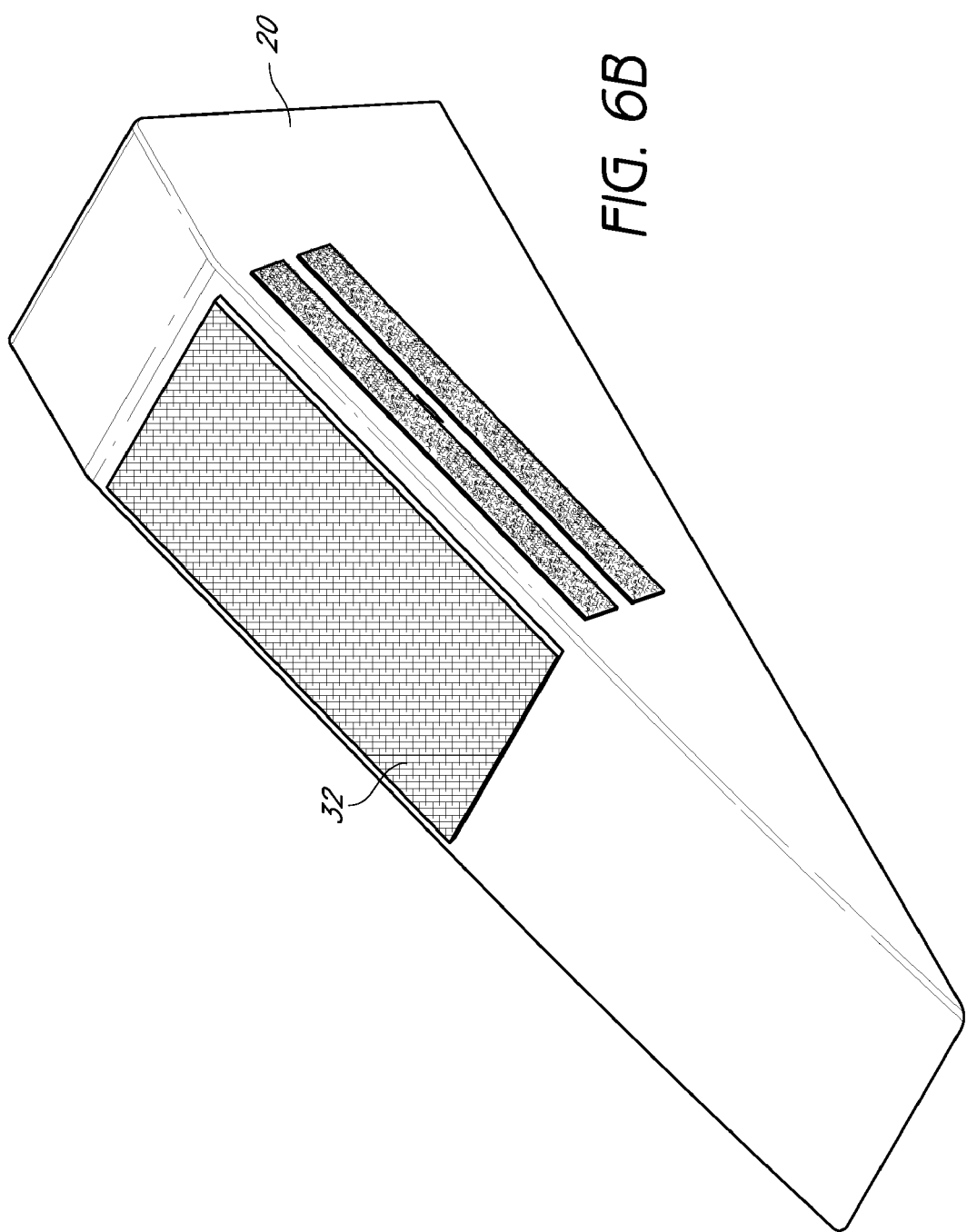

ARM POSITIONER FOR DIAGNOSTIC PROCEDURE

BACKGROUND OF THE INVENTION

1. Field of the Invention

The present application relates to arm positioning devices, and, more specifically, to arm positioning devices to maintain an arm in a given position for a medical procedure.

2. Description of the Related Art

When a patient requires magnetic resonance imaging (MRI) or another diagnostic scan of the upper arm or shoulder joint, typically, for optimal imaging, the patient is asked to position his arm such that his forearm is inclined and his hand is positioned with the lower wrist and palm facing upwards. The patient must maintain that palm-up position while the diagnostic scan is conducted. An MRI or other scan can take approximately 30 minutes or more. During this time, many patients have a tendency to rotate their palms away from the upward-facing orientation, which can compromise the images obtained from the scan and require additional time to complete the imaging.

SUMMARY OF THE INVENTION

In certain aspects, a system for maintaining an arm of a patient in position for a diagnostic procedure is disclosed. The system comprises a positioning block and a restraint device. The positioning block has an upper surface to receive the arm of the patient. The restraint device is configured to be worn by the patient. The restraint device is configured to be coupled to the positioning block to maintain a position of the arm of the patient in a desired orientation relative to the positioning block. In some embodiments, the restraint device can have a plurality of orientations relative to the positioning block. The positioning block and the restraint device are composed of materials that are suitable for use in a medical diagnostic machine.

In other aspects, a system for positioning the arm of a patient for a diagnostic procedure is provided. The system comprises a positioning block and a restraint member (e.g., a loop or glove, which, in some embodiments, can be adjustable in size). The positioning block can have an inclined upper surface. The restraint member is configured to receive one or more digit on a hand or another portion of the hand (e.g. the palm) or wrist of the patient. The restraint member has an attachment device positioned thereon. The positioning block comprises at least one attachment device configured to couple to the attachment device on the restraint member to retain the arm of the patient in a desired position with respect to the positioning block. The attachment device on the positioning block is configured such that the restraint member can be repositioned to retain the arm in a second desired position with respect to the positioning block. In one preferred form, the attachment device or the positioning block has an elongated surface along which the restraint member can be attached.

In other aspects, a method of retaining an arm of a patient in a desired position for a diagnostic procedure is provided. The method comprises positioning a digit, hand, or wrist of the patient in a retention loop, orienting the arm of a patient on a positioning block, coupling the retention loop to the positioning block, and activating a diagnostic device. The diagnostic device is activated to perform a diagnostic procedure on the patient without interference by the positioning block and the retention.

BRIEF DESCRIPTION OF THE DRAWINGS

These and other features, aspects, and advantages of various embodiments of the inventions will now be briefly described. The illustrated embodiments, however, are merely exemplary and are not intended to be limiting. The drawings include the following nine figures.

FIG. 6A is a perspective view of an embodiment of positioning block for use in the arm positioning system of FIG. 1 having a removable jacket;

FIG. 6B is a perspective view of another embodiment of positioning block for use in the arm positioning system of FIG. 1 having a removable upper pad;

DETAILED DESCRIPTION OF THE PREFERRED EMBODIMENT

Arm Positioning System

Figure 1:
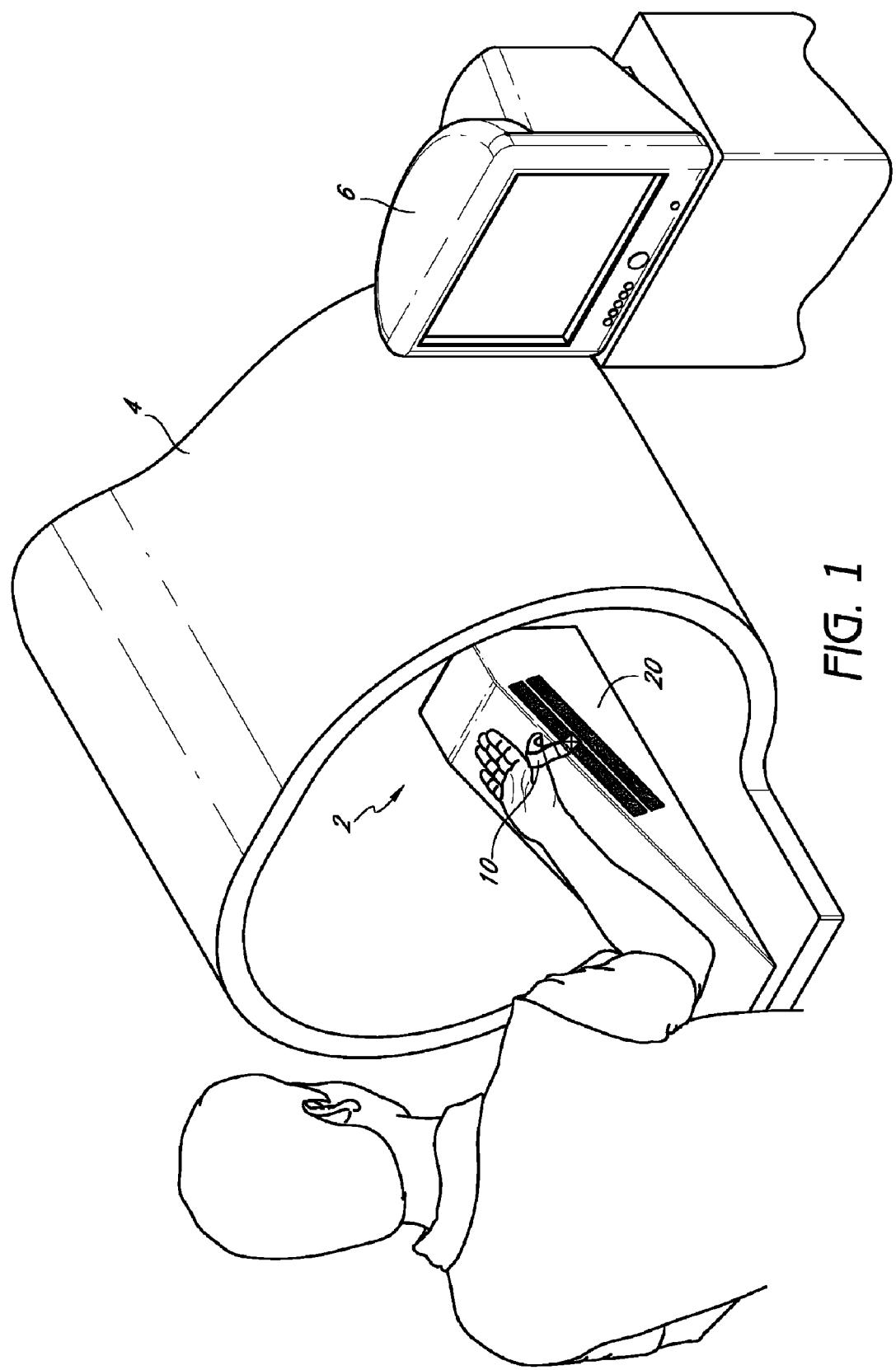
FIG. 1 is a perspective view of a patient's arm placed in an arm positioning system, which is configured in accordance with a preferred embodiment of the present invention, for a diagnostic procedure.

With respect to FIG. 1, a preferred embodiment of an arm positioning system 2, which can be used in a medical diagnostic procedure, is illustrated. As further described below, in various embodiments, the arm positioning system 2 can include a restraint device 10 and a positioning block 20. In certain embodiments, the restraint device 10 and the positioning block 20 can be configured to maintain the arm of a patient in a desired position. In some embodiments, the restraint device 10 and the positioning block 20 can be configured to maintain the patient's forearm at an incline with a palm of the patient's hand in a supine position (facing upward), a pronated position (facing downward), or at another orientation.

In certain embodiments, both the restraint device 10 and the positioning block 20 are configured to be used in a diagnostic device 4, such as a magnetic resonance imaging (MRI) device, a computed tomography (CT) scan device, an X-ray device, an ultrasound device, or another diagnostic device (e.g. an imaging device). Thus, the restraint device 10 and the positioning block 20 preferably are constructed of materials that do not interfere with the diagnostic device. In some embodiments, neither the restraint device 10 nor the positioning block 20 includes ferrous metals, or other materials that are opaque with respect to a diagnostic device used. In other embodiments, such materials can be used, but positioned outside an intended viewing region, such as along a periphery or at an end of the arm positioning block 20. The diagnostic device 4 can be operatively coupled to a processor 6, in some embodiments having a display or other output.

As illustrated in FIG. 1, the patient is shown sitting adjacent a diagnostic device 4 with an arm placed in a diagnostic area of the device. The arm positioning system 2 can also be used to position a patient's arm in a diagnostic device 4 in other positions and orientations, for example, in a position next to a patient's body where the patient is lying down in a diagnostic area of the device in either a prone position or a supine position.

In certain embodiments, the arm positioning system 2 can be configured to facilitate positioning of the patient's arm in a first desired position with respect to the positioning block 20 and subsequent repositioning of the patient's arm in a second position with respect to the positioning block 20. As discussed in further detail below, in some embodiments, the arm positioning system 2 can be configured to allow the patient's arm to be positioned in many different positions, and can accommodate variations among arm, hand, and digit sizes of patients.

Figure 2:
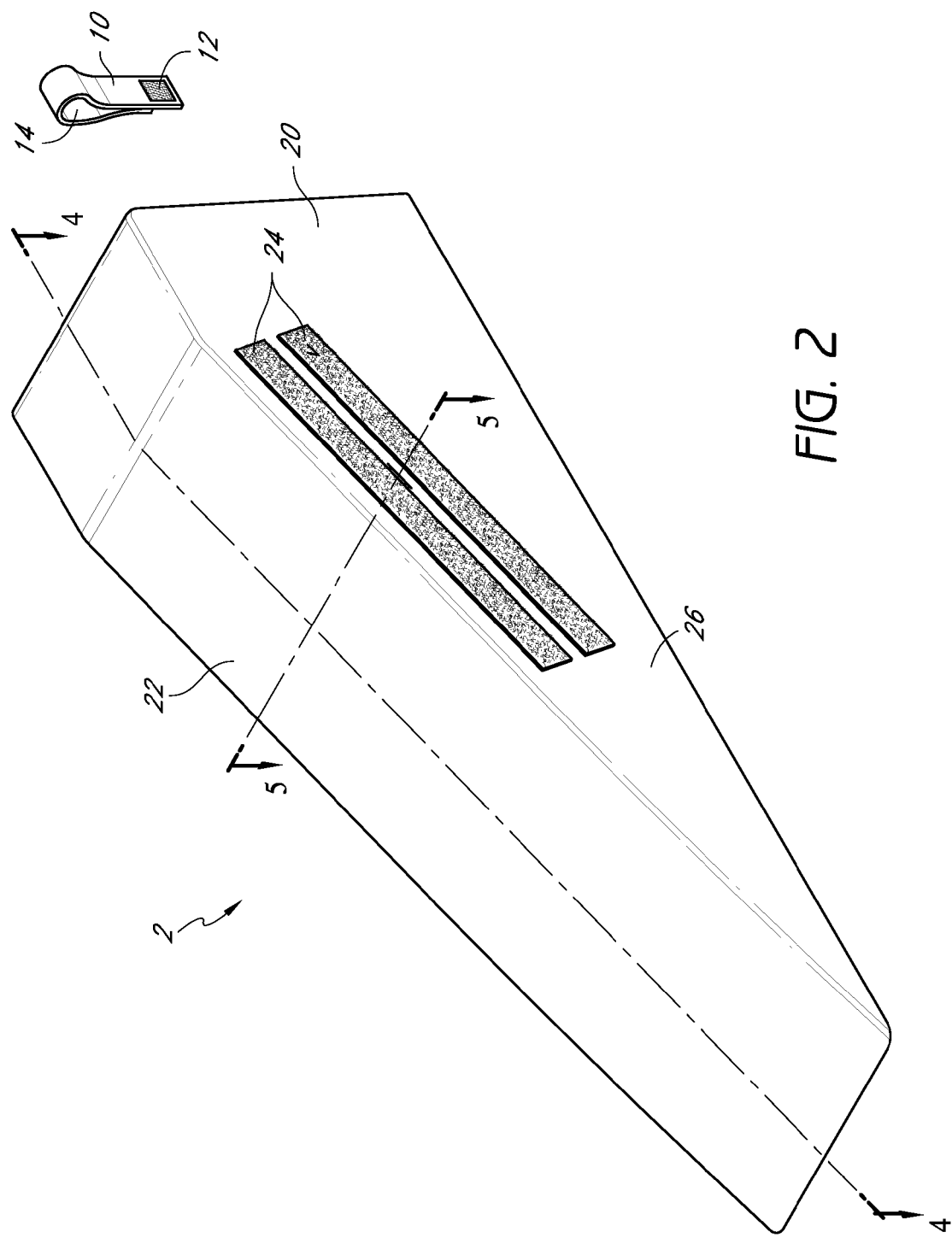
FIG. 2 is a perspective view of the arm positioning system of FIG. 1 with a retention loop thereof shown apart from a positioning block.

With reference to FIG. 2, an embodiment of arm positioning system 2 is illustrated. The illustrated embodiment includes a restraint device 10 and a positioning block 20. As discussed in further detail below, the restraint device 10 preferably is configured to be coupled to the positioning block 20 in multiple positions and/or orientations, allowing the arm of a patient to be positioned as desired for a medical diagnostic procedure.

With reference to FIG. 2, in the illustrated embodiment, the positioning block comprises a generally prismatic, e.g. parallelepiped, block having an upper surface 22 and a side surface 26 on which an attachment surface is disposed. In the illustrated embodiment, the upper surface 22 is generally inclined such that it extends between a lower edge adjacent the patient and a higher edge away from the patient. Advantageously, this inclined surface provides support for the forearm of a patient with the wrist positioned higher than the elbow, as can be desired for certain diagnostic procedures on the upper arm and shoulder. In other embodiments of arm positioning system 2, the upper surface 22 can be configured to support the arm of a patient in a different orientation. For example, in some embodiments, the incline of the upper surface 22 can be reversed such that the wrist of the patient is lower than the elbow. In other embodiments, the upper surface 22 of the positioning block 20 can be substantially level to support the patient's arm in a substantially level orientation from elbow to wrist.

In some embodiments, the positioning block 20 can have a bottom surface. The positioning block can be configured such that the block can be repositioned with the bottom surface facing up such that it can support the forearm of the patient. In some embodiments, the positioning block can be configured such that with the bottom surface facing upwards, the positioning block presents a different angle of incline than with the upper surface facing upwards. In some embodiments, the positioning block can be a prism having a triangular cross section. The block can be configured such that the upper surface and the bottom surface have substantially the same length so that either surface can be used to support the arm of the patient.

In some embodiments, either the upper surface, the bottom surface, or both, of the positioning block can be contoured to maintain the forearm or wrist of the patient in a desired rotated position. In some embodiments, the contouring can include a concave channel that can extend along at least a portion of a surface of the positioning block. In other embodiments, the contouring can include one or more convex protrusions extending along at least a portion of a surface of the positioning block. In some embodiments, the contouring can include a concavity having a convex protrusion therein, each extending along at least a portion of a surface of the positioning block. In some embodiments, the upper surface can include a first contour, while the bottom surface can include a second contour different from the first contour such that when the block is reoriented with the bottom surface facing upwards, a the second contour is presented to the patient.

With continued reference to FIG. 2, the attachment surface on the positioning block 20 can comprise one or more fastening strips 24. In some embodiments, the fastening strips 24 can be one of a hook fastener or a loop fastener in a hook and loop fastener system. The restraint device 10 can include a mating attachment surface comprising fastening strip 12 including a mating hook or loop fastener. Advantageously, hook and loop fasteners can be easily attached, removed, and repositioned, and can offer sufficient coupled strength to maintain a patient's arm and wrist in a desired position. In other embodiments, the attachment surfaces on the restraint device 10 and the positioning block 20 can be different fasteners such as reusable adhesive strips to mate to other adhesive strips or an adhesive mating surface, snaps, mating tab fasteners, or other types of fasteners. Desirably, the attachment surfaces allow for rapid, easy attachment, removal, and repositioning of the restraint device and the positioning block. The attachment surfaces can also be integrated with outer surfaces of the positioning block 20.

Positioning Block

Figure 3:
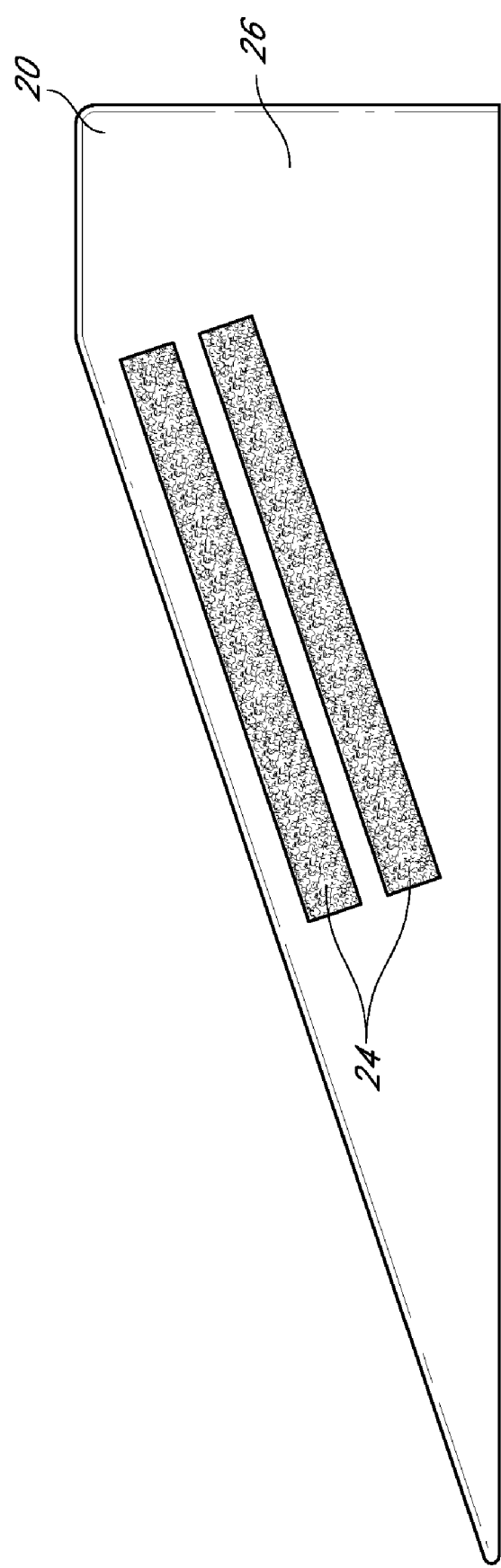
FIG. 3 is a side view of the positioning block of the arm positioning system of FIG. 1.

With respect to FIGS. 2 and 3, in the illustrated embodiments, the positioning block 20 includes two fastening strips 24 disposed on both side surfaces 26 of the block 20, so as to be used for both right and left hands and arms. However, other embodiments can use only one strip. The fastening strips 24 can be generally elongate strips having a length that is relatively large compared to a width of the strip. In some embodiments, the length of the fastening strips 24 can extend along substantially an entire length of the side surface 26 of the block 20. In other embodiments, the fastening strips 26 can extend along a portion of the side surface 26 of the block such as one half of the length, one fourth of the length, or another portion. In some embodiments, the fastening strips 24 need not be positioned on a side surface of the positioning block 20, but can be positioned on the upper surface 22, or a front or rear surface of the positioning block 20. In some embodiments, a fastening surface can cover all of, or a portion of a surface of the positioning block 20 and need not be a strip of material.

With respect to FIGS. 2 and 3, as illustrated, the fastening strips 24 are positioned such that axes defined by the lengths thereof are generally parallel to an upper edge of the side surface 26 of the block 20. Further, each fastening strip can be generally parallel to the other fastening strip 24. The upper edge of the side surface 26 of the block can be defined by the interface of the side surface 26 with the upper surface 22 such that the orientation of the fastening strips 24 with respect to the positioning block 20 corresponds to an angle of incline of the upper surface 22 of the positioning block 20. Advantageously, an inclined orientation of the fastening strips 24 generally corresponding to the upper surface 22 of the block allows a patient's arm to be positioned at a desired inclination regardless of the length of a patient's arm along the upper surface 22 of the block.

While the illustrated perspective views show fastening strips 24 along a right side of the positioning block 20, which allow the positioning of a patient's right arm, it is contemplated that in various embodiments, a positioning block 20 can have attachment surfaces such as fastening strips 24 on either or both of the sides thereof. Advantageously, a positioning block 20 with fastening strips on both sides thereof can allow either arm of the patient to be positioned on the same positioning block 20. Furthermore, it is contemplated that in some embodiments, the attachment surface can include fastening strips 24 disposed on the upper surface of the positioning block 20.

While the illustrated embodiments include two generally parallel fastening strips 24, in other embodiments, different arrangements of fastening strips are contemplated. For example, in some embodiments, there can be more or fewer than two fastening strips 24. In some embodiments, the fastening strips 24 can be transverse (e.g. skewed) to one another. In some embodiments, the fastening strips 24 can be skewed relative to the upper edge of the side surface of the block 20. In some embodiments, substantially the entire side surface 26 of the block 20 can be covered with an attachment surface, allowing the retention device 10 to be coupled to the positioning block 20 at substantially any location on the side surface 26. In other embodiments, all or part of the upper surface, front, or back surface can include an attachment surface.

Figure 4A:
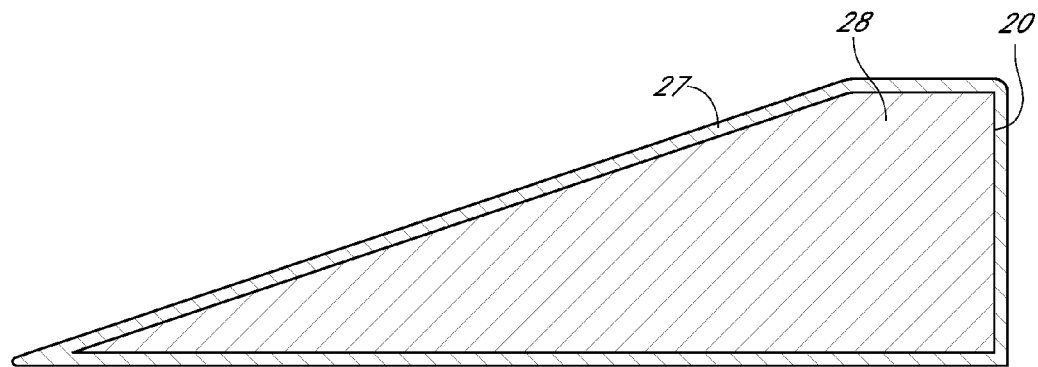
FIG. 4A is a longitudinal cross-sectional view of the positioning block of FIG. 3.
Figure 4B:
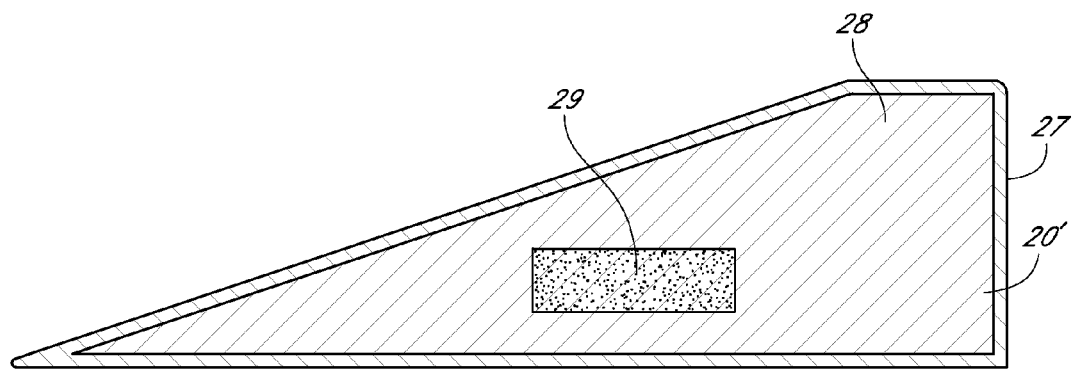
FIG. 4B is a longitudinal cross-sectional view of another embodiment of a positioning block configured similarly to that shown in FIG. 3.

With reference to FIGS. 4A and 4B, longitudinal cross sectional views of several embodiments of positioning block 20 are illustrated. In the embodiments of FIG. 4A, the positioning block 20 preferably comprises an outer coating 27 surrounding a foam body 28. The outer coating 27 can be a natural or synthetic rubber-like coating that can be applied by being brushed on, sprayed on, dip molded, or by another suitable method. Advantageously, the outer coating 27 can be water resistant, swabbable, and resistant to degradation from chemical cleansers. Thus, the outer coating 27 can provide a hygienic surface that can be periodically cleaned and disinfected (e.g., between uses). The outer coating 27 can also provide a barrier to prevent water or other liquids from entering the foam body 28.

With reference to FIG. 4A, the foam body 28 of the positioning block 20 can be a polyurethane foam or other foam (e.g., open-cell, closed cell, reticulated, etc.). The foam can have properties such that it is sufficiently rigid to support a patient's arm, but soft enough to be comfortable for the patient for the length of a typical diagnostic session. In some embodiments, the body 28 can be constructed from materials other than foam.

With reference to FIG. 4B, another embodiment of positioning block 20' is illustrated that includes an outer coating 27 and foam body 28 as discussed above with respect to FIG. 4A, and a weighting member 29. The weighting member 29 desirably has a high density relative to the foam body 28. Advantageously, the weighting member 29 can enhance the stability of the positioning block 20' and prevent the patient from inadvertently lifting or tipping the positioning block 20 during a diagnostic procedure.

Desirably, the weighting member 29 is composed of a material that does not interfere with the diagnostic procedure. Accordingly, in some embodiments, it can be desirable that the weighting member 29 does not include ferrous metals. In some embodiments, the weighting member 29 can include a volume of sand. The sand can be encapsulated in a rubber shell or other capsule positioned in a cavity in the foam body 28. Advantageously, sand is relatively dense, readily available, and relatively inexpensive. In other embodiments, the weighting member 29 can include a non-ferrous metal such as a bar of titanium, a titanium alloy, or another non-ferrous metal or metal alloy. In other embodiments, the weighting member can include a liquid or gel material that can be encapsulated and positioned in a cavity in the foam body. Although the illustrated embodiments illustrate the weighting member in a generally central location within the body 28, in some embodiments, the weighting member can be located elsewhere in the body 28. For example, the weighting member 29 can be positioned at a lower portion of the body 28, thus forming a base for the positioning block 20'.

Figure 5:
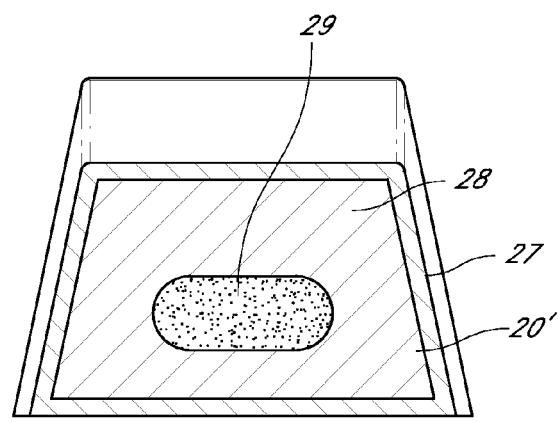
FIG. 5 is a transverse cross-sectional view of the positioning block of FIG. 4B.

With reference to FIG. 5, a transverse cross section of the positioning block 20' of FIG. 4B is illustrated. In the illustrated embodiment, the positioning block 20' has a generally trapezoidal cross section with a lower surface defining a base that is relatively wide compared to the upper surface of the block 20'. Advantageously, this relatively wide base enhances the stability of the positioning block 20' as it reduces the chance that a patient can inadvertently tip the block 20' laterally. Other embodiments of positioning block 20, such as those of FIG. 4A which do not include a weighting member 29, can also have a generally trapezoidal transverse cross-sectional profile. In other embodiments, the base can include a relatively high friction surface, such as a roughened surface or a textured surface to further enhance the stability of the positioning block 20'. While the illustrated embodiments include a generally trapezoidal cross-section block, it is contemplated that in other embodiments, the positioning block 20, 20' can have another cross-sectional profile, such as a substantially rectangular transverse cross-sectional profile.

With reference to FIG. 5, the upper surface 22 of the positioning block 20' is illustrated as a substantially planar surface. It is contemplated that in other embodiments, the upper surface 22 of the positioning block 20, 20' can have a contoured surface. In some embodiments, the upper surface 22 can be lower near a mid section of the surface 22 than at the edges (e.g. concave). Such a contoured upper surface can advantageously reduce the risk that the patient's arm can slip off of the positioning block 20 and can enhance comfort to the patient.

With reference to FIGS. 6A and 6B, embodiments of positioning blocks 20 are illustrated having removable surfaces to maintain the cleanliness of the positioning block 20 where the positioning block 20 is used for multiple patients. As noted above with respect to FIGS. 4A and 4B, in some embodiments the positioning block can include a swabbable outer cover 27 (FIGS. 4A, 4B). The removable surfaces illustrated in FIGS. 6A and 6B and described in further detail below can further enhance cleanliness by providing each successive patient with a newly cleaned surface on which his arm will be supported. The removable surfaces can further increase the speed with which the positioning block 20 can be prepared for successive patients by being rapidly changeable without requiring the application of chemical cleansers.

As illustrated in FIG. 6A, in some embodiments, in addition to, or in place of the swabbable outer cover, the positioning block can include a removable jacket 30. The jacket 30 can be disposable such that at each diagnostic session with the arm positioning system, a new jacket 30 is provided. In some embodiments, the jacket is composed of a material that substantially prevents the passage of liquids therethrough to the positioning block 20. In other embodiments, the jacket 30 can be constructed of a paper or fabric that is not resistant to liquid flow therethrough. The jacket 30 can be shaped to fit around at least a portion of the positioning block 30 and can include an elastic band, zipper, mating hook and loop fastener, adhesive strip, or other closable or reclosable portion to allow the jacket 30 to be placed on the positioning block 20 and maintained in position. Once a diagnostic session has been completed, the jacket 30 can be disposed of or cleaned (e.g. laundered) for reuse.

In some embodiments, as illustrated in FIG. 6B, the positioning block 20 can include a support pad 32 extending over at least a portion of the upper surface of the positioning block. In various embodiments, the support pad 32 can be suitable for a use in a single diagnostic session, or can be suitable for reuse. In various embodiments, the support pad 32 can extend over some or all of the upper surface of the positioning block 20 on which the arm of the patient rests. In other embodiments, the support pad can cover other surfaces of the positioning block 20 in addition to at least a portion of the upper surface. In some embodiments, the support pad 32 can include an elastic strap, an adhesive strip, or a mating fastener, to maintain the position of the support pad 32 on the positioning block 20. While the support pad 32 is illustrated as being generally flat, in some embodiments, it can have other configurations such as for example, a concave surface. In some embodiments, the support pad can be flat, but be sufficiently flexible to conform to surface contours of the positioning block 20.

Restraint Device

Figure 7A:
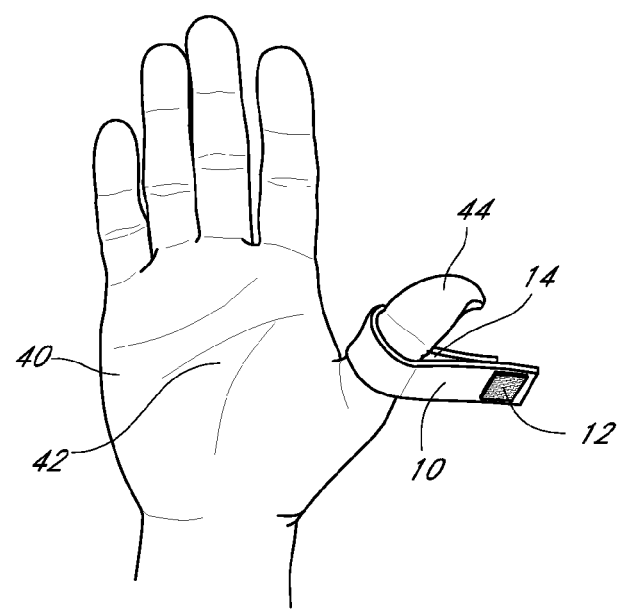
FIG. 7A is a perspective view of one embodiment of restraint member or device for use in the arm positioning system of FIG. 1 positioned about the thumb of a patient.
Figure 7B:
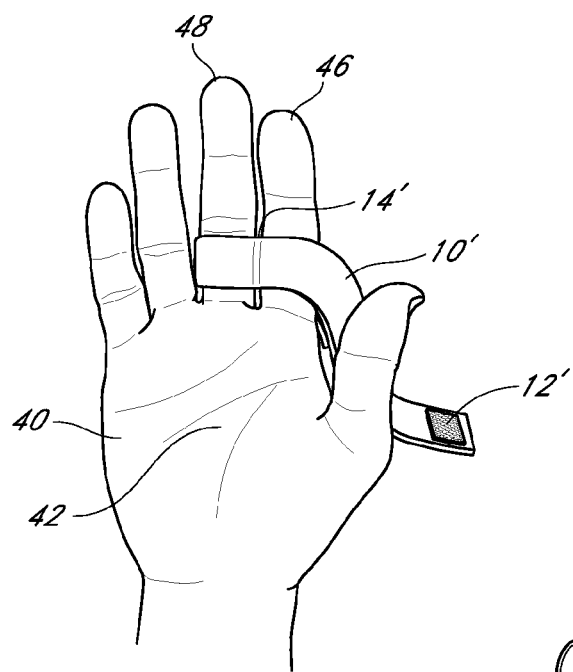
FIG. 7B is a perspective view of another embodiment of restraint device for use in the arm positioning system of FIG. 1 positioned about the index and middle fingers of a patient.
Figure 7C:
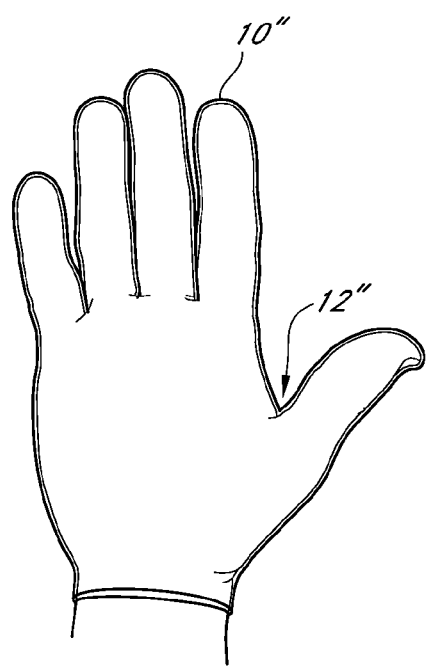
FIG. 7C is a perspective view of another embodiment of restraint device for use in the arm positioning system of FIG. 1 positioned about the hand of a patient.

With reference to FIGS. 7A-7C, three embodiments of restraint device 10, 10', 10" are shown to illustrate the various forms that the restraint device can take. The restraint device generally maintains the position and orientation of the forearm of a patient relative to the positioning block, and can take various forms, some of which are illustrated below. Desirably the embodiments of restraint device 10, 10', 10" are composed of materials that do not interfere with medical diagnostic devices. In some embodiments, the restraint devices 10, 10', 10" can be composed of materials that are sufficiently resistant to elongation under the tension loading imposed thereon that they can maintain a patient's hand in a desired position. For example, the restraint devices 10, 10', 10" can be composed of leather, natural or synthetic fabrics such as cotton or nylon, natural or synthetic rubbers, and plastic materials. In some embodiments, the restraint devices 10, 10', 10" can be composed of a material having elasticity such as a natural or synthetic rubber material. One or more elastic restraint devices 10, 10', 10" can be used to place ligaments or other soft tissue of the patient in tension, such as for example by being arranged to pull the patient's thumb laterally, or to pull apart two fingers (such as, for example, one finger being pulled medially by one elastic restraint device and one finger being pulled laterally by another elastic restraint device).

FIG. 7A illustrates a restraint device 10 comprising a thumb strap. FIG. 7B illustrates a restraint device 10' comprising a multi-finger strap. FIG. 7C illustrates a restraint device 10" comprising a glove. In some embodiments, the restraint device need not receive a digit of the patient, rather, it can wrap around the palm or wrist of the patient.

FIGS. 7A-7C illustrate various embodiments of restraint device 10, 10', 10" as applied to the right hand 40 of a patient to maintain the palm 42 in a supine or palm-up orientation. However, it is contemplated that similar restraint devices 10, 10', 10" can be used to maintain a left hand of a patient in a palm-up orientation. Furthermore, similar restraint devices can be used to maintain the hand and arm of a patient in other orientations for different diagnostic or surgical procedures where the palms-up orientation is not a desired position.

As illustrated in FIG. 7A, in some embodiments, the restraint device 10 in an arm positioning system 2 (FIG. 1) can comprise a thumb strap. For various upper arm and shoulder diagnostic scans, it can be desirable to position a patient's arm with the elbow at an inclined angle and the hand 40 rotated such that the palm 42 is facing up. As this hand and arm orientation is different from a natural resting position of a hand and arm, it can be difficult for a patient to maintain this position during a diagnostic procedure. As a patient tries to maintain a palm-up position, the patient's arm and hand will tend to rotate towards a thumb-up orientation. Therefore, by restraining the thumb 44 with a thumb strap, a desired palm-up orientation can be maintained.

With reference to FIG. 7A, the thumb strap comprises a loop 14 configured to receive a single digit of the patient's hand. Desirably, the loop 14 is large enough to receive the patient's thumb 44. The thumb strap also comprises an attachment surface such as a fastening strip 12. As described above, in some embodiments the fastening strip 12 can comprise one of a hook and a loop fastener configured to mate with the corresponding hook or loop fastening strip on the positioning block (see FIGS. 1 and 2).

It is contemplated that in some embodiments, a single-digit strap, such as the restraint device 10 illustrated in FIG. 7A, can be worn on another finger of the patient. For maintaining the patient's hand in a palm-up position, desirably, the strap would be worn on the index or middle finger to resist pronation of the hand towards a thumb-up orientation. In some embodiments, a patient's hand can be maintained in position with more than one restraint device 10, 10'. For example, the patient could wear a single-digit strap restraint device 10 over a thumb, and a single digit strap restraint device 10 over a little finger, each of the restraint devices 10 being coupled to the positioning block 20 (see FIG. 1). In other embodiments, the patient could wear another combination of single and multiple digit restraint devices 10, 10' over various digits. Thus, patients who have finger injuries such as broken or sprained fingers can use the arm positioning device without the restraining device 10, 10' placing additional stress on the injured finger or fingers.

With reference to FIG. 7B, another embodiment of restraint device 10' including a multi-digit strap is illustrated. In the illustrated embodiment, the multi-digit strap is shown positioned around the index and middle finger of a patient's hand. In other embodiments, the multi-finger strap can be positioned around other fingers, or around the thumb and index finger. Advantageously, a restraint device 10' restraining the movement of the index and middle fingers tends to prevent the tendency of the patient's hand 40 to rotate to a thumb-up orientation. The multi-digit restraint device 10' includes a loop 14' configured to receive more than one of the patient's digits. The restraint device further comprises an attachment surface such as a fastening strip 12' as described above with respect to the thumb strap.

With reference to FIG. 7C, another embodiment of restraint device 10" comprising a glove is illustrated. The glove can include an attachment surface such as a fastening strip 12" positioned on a surface thereof corresponding to the side of the patient's hand opposite the palm. In some embodiments, a side of the glove can be substantially covered in a fastening material such as a hook or loop surface of a hook and loop fastener. Where the glove is configured to be worn on either hand, the restraint device 10" can include a fastening strip 12" or attachment surface on both the palm side and opposite side. The restraint device 10" can couple to corresponding attachment surfaces on a positioning block 20, desirably positioned on an upper surface 22 of the positioning block 20 (see FIG. 2). Advantageously, a restraint device 10" comprising a glove can distribute restraining force over a larger portion of the patient's hand than a digit strap, and may enhance comfort for some patients.

While the illustrated restraint device is a whole hand glove, it is contemplated that in other embodiments, the glove could cover a portion of the patient's hand such as for example, a tab-like strap restraining some or all of the patient's fingers or a glove that does not cover the patient's fingers past a first knuckle. In some embodiments, a restraint device can include a relatively rigid member configured to retain one or multiple digits of the wearer. For example, a relatively rigid bar formed of a plastic material can include apertures through which one or more digits of a patient are placed. This bar can include a fastening strip on a surface thereof, or it can be coupled to a restraint strap to removably couple the bar to an attachment surface on the positioning block. Some arm positioning systems 2 (FIG. 1) can include multiple sizes of restraint device 10" gloves such that a wide variation among hand and digit sizes of patients (for example, child-sized gloves, medium, and large gloves) can be accommodated with the arm positioning system.

Arm Positions

Figure 8:
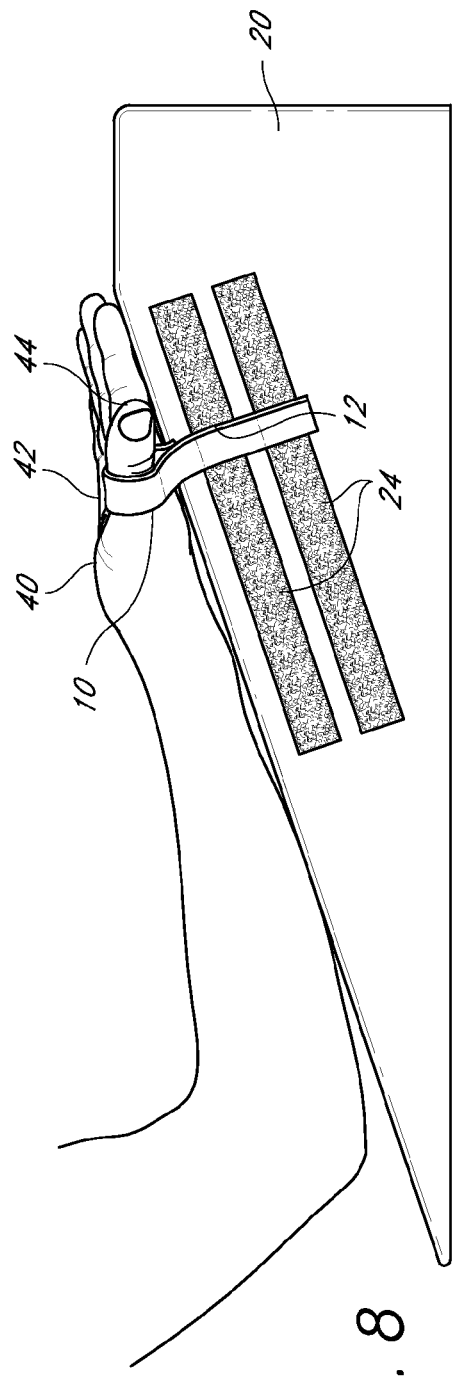
FIG. 8 is a side view of the arm positioning system of FIG. 1 with a patient's arm maintained in a first position.
Figure 9:
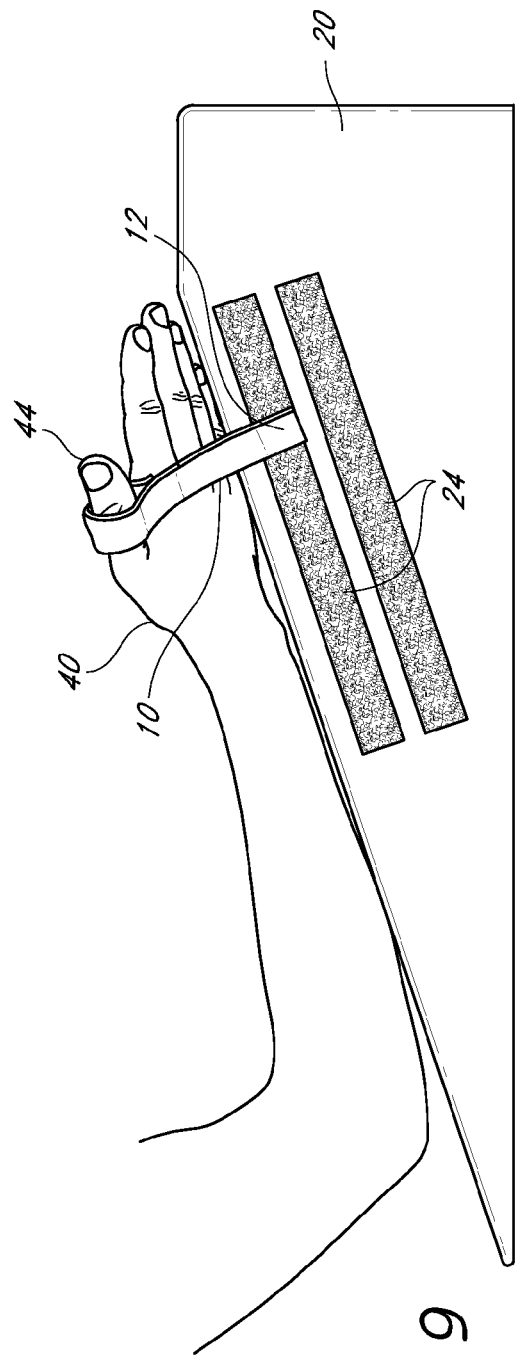
FIG. 9 is a side view of the arm positioning system of FIG. 1 with a patient's arm maintained in a second position.

FIGS. 8 and 9 illustrate the arm positioning system used to position a patient's arm in two positions. FIG. 8 illustrates the patient's arm positioned in a first desired position, palm facing upwards. FIG. 9 illustrates the patient's arm positioned in a second desired position, palm facing upwards and slightly raised from the upper surface of the positioning block 20.

To position the patient's hand in a positioning a first desired position, as shown in FIG. 8, a digit of the patient, such as the thumb 44, is inserted in the retention device 10. As discussed above, in other embodiments, the patient's hand can be inserted in a different retention device 10 such as a multi-digit retention device 10' (FIG. 7B) or glove-like retention device 10" (FIG. 7C).

The patient's arm is then oriented in a desired position with respect to the positioning block 20. For certain upper arm and shoulder diagnostics, the patient's arm is oriented with a bend at the elbow, the forearm at an incline with respect to horizontal, and palm facing up, as illustrated in FIG. 8. The upper surface 22 of the positioning block 20 can receive the patient's arm: the patient's arm can be positioned resting on or displaced some distance from the upper surface 22 of the positioning block 20. Where the upper surface 22 is contoured, (e.g. concave), the patient's arm can rest on the positioning block 20 in the concavity.

The retention device 10 is then coupled to the positioning block 20. In the illustrated embodiment, the retention device 10 and the positioning block 20 each comprise attachment surfaces having fastening strips 12, 24 disposed thereon. Coupling the retention device 10 to the positioning block 20, therefore, can comprise fastening the hook fastener to the loop fastener of the hook and loop fastener. As noted above, in other embodiments, the attachment surfaces can comprise other fastening surfaces or mechanisms. Advantageously, in the illustrated embodiment, the elongate fastening strips 24 on the positioning block 24 accommodate arm positioning for variability among arm lengths of different patients.

Once the patient's arm is in a desired position and restrained by the coupling of the restraint device 10 with the positioning block 20, medical diagnostic staff or professionals can activate a diagnostic device such as an MRI machine, a CT scanning machine, an X-ray machine, or an ultrasound machine. The diagnostic device can perform a diagnostic scan of the patient's arm. As noted above, desirably, the positioning block 20 and the retention loop 10 are configured not to interfere with the diagnostic device.

In some diagnostic procedures, it can be desirable to reposition the patient's arm to a different position where the forearm is at a different incline than the positioning block 20, or is raised from the surface of the positioning block 20, unlike the first desired position shown in FIG. 8. As noted above, the positioning block can include a parallel fastening strip 24 to allow repositioning of the patient's arm at a known vertical offset from the first position. In FIG. 9, the patient's arm is illustrated repositioned into a second desired position that is vertically offset from the first desired position. In other embodiments, the attachment surface of the positioning block 20 can comprise markings or other indicia to indicate attachment locations for the retention device 10 for one or more desired positions of a patient's arm.

To reposition the patient's arm into the second desired position, shown in FIG. 9, from the first desired position, shown in FIG. 8, the retention device 10 is first decoupled from the positioning block 20. In embodiments of arm positioning system including repositionable fasteners, such as hook and loop fasteners, for the attachment surfaces of the retention device 10 and the positioning block 20, decoupling includes pulling the retention device 10 away from the positioning block 20. The patient's arm is then reoriented in a second desired position. Finally, the retention device 10 is recoupled to the positioning block 20 to maintain the patient's arm in the second desired position. In the illustrated embodiment, the repositioning includes recoupling the restraint device 10 to a different fastening strip 24 on the positioning block that is offset from the fastening strip 24 to which the restraint device 10 was coupled in the first desired position.

Although the arm positioning system has been disclosed in the context of certain preferred embodiments and examples, it will be understood by those skilled in the art that the present disclosure extends beyond the specifically disclosed embodiments to other alternative embodiments and/or uses of the arm positioning system and obvious modifications and equivalents thereof. In addition, while a number of variations of the arm positioning system have been shown and described in detail, other modifications, which are within the scope of the inventions, will be readily apparent to those of skill in the art based upon this disclosure. It is also contemplated that various combinations or sub-combinations of the specific features and aspects of the embodiments may be made and still fall within the scope of the disclosure. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above, but rather should be defined by a fair reading of the specification and the claims that follow.

What is claimed is:

1. A system for maintaining an arm of a patient in position for a diagnostic procedure of at least one of a shoulder and upper arm, the system comprising:
  a positioning block comprising:
    an inclined upper surface, the inclined upper surface being configured to support an arm of a patient, including an elbow and hand of the patient,
    a first attachment surface located on a first side of the positioning block, and
    a second attachment surface located on a second side of the positioning block; and a restraint device couplable to the first attachment surface of the positioning block and configured to wrap about at least a portion of the patient and maintain the hand of the patient in a substantially palm-up position during a diagnostic procedure of at least one of a shoulder and upper arm of the patient, wherein the restraint device can be repositioned to a different location of the first attachment surface to maintain the hand of the patient in a second desired position with respect to the positioning block, and the positioning block and the restraint device are composed of materials that are suitable for use in a medical diagnostic machine.

2. The system of claim 1, wherein the positioning block comprises a foam block.

3. The system of claim 2, wherein the positioning block comprises a weighting member.

4. The system of claim 3, wherein the weighting member comprises sand.

5. The system of claim 1, wherein the positioning block comprises a removable jacket.

6. The system of claim 1, wherein the positioning block comprises a swabbable outer surface.

7. The system of claim 1, wherein the positioning block comprises a fastening strip.

8. The system of claim 7, wherein the fastening strip comprises one of a hook fastener and a loop fastener.

9. The system of claim 8, wherein the restraint device is configured to mate with the fastening strip and the restraint device comprises the other of the hook fastener and the loop fastener.

10. The system of claim 7, wherein the positioning block comprises a second fastening strip offset from the fastening strip.

11. The system of claim 1, wherein the restraint device comprises a strap having a loop configured to retain one or more digits of the hand of the patient.

12. The system of claim 11, wherein the restraint device comprises a strap having a thumb loop.

13. The system of claim 1, wherein the restraint device comprises a glove.

14. The system of claim 1, wherein the positioning block and the restraint device are constructed of non-ferrous materials.

15. A system for positioning the arm of a patient for a diagnostic procedure comprising:
    a positioning block having an inclined upper surface configured to support a hand and elbow of a patient; and
    a restraint device configured to receive at least a portion of a hand of the patient, the restraint device having an attachment surface positioned thereon, wherein
    the positioning block comprises at least a first attachment surface located on a first side surface of the positioning block configured to couple to the attachment surface on the restraint device to retain the hand of the patient in a substantially palm-up position with respect to the positioning block, and a second attachment surface disposed on a second side surface of the positioning block, and wherein
    the first attachment surface on the positioning block is configured such that the restraint device can be repositioned to retain the hand of the patient in a second desired position with respect to the positioning block.

16. The system of claim 15, wherein the attachment surfaces on the restraint device and the positioning block each comprise one of a hook fastening surface and a device fastening surface.

17. The system of claim 15, wherein the arm, when in the desired position, is positioned a first distance from a substantially flat upper surface of the positioning block and, when in the second desired position, is positioned a second distance from the substantially flat upper surface of the positioning block, the second distance being greater than the first distance.

18. The system of claim 15, wherein the first attachment surface and the second attachment surface comprise elongated attachment surfaces and the first attachment surface and the second attachment surface define a longitudinal axis, wherein the longitudinal axes of the first attachment surface and the second attachment surface are substantially parallel to one another.

19. The system of claim 15 wherein the positioning block further comprises a third attachment surface and a fourth attachment surface, wherein the first and third attachment surfaces are disposed on the first side surface of the positioning block; the second and fourth attachment surfaces are disposed on the second side of the positioning block; wherein each of the attachment surfaces of the positioning block comprises an elongate strip defining a longitudinal axis.

20. The system of claim 19, wherein the longitudinal axes of the first and second attachment surfaces are substantially parallel to each other and the longitudinal axes of the third and fourth attachment surfaces are substantially parallel to each other.

21. A method of retaining an arm of a patient in a desired position for a diagnostic procedure comprising:
    positioning at least one digit of a hand of the patient in a retention device;
    orienting the hand of the patient in a desired position on an upper surface of a positioning block;
    coupling an interface surface of the retention device with an interface surface of the positioning block to maintain the hand in the desired position wherein the interface surface of the positioning block is located on a side surface of the positioning block; and
    performing a diagnostic procedure on at least one of a shoulder and upper arm of the patient.

22. The method of claim 21 wherein the coupling the interface surface of the retention device with the interface surface of the positioning block comprises coupling a hook fastening surface with a loop fastening surface to couple the retention device to the positioning block.

23. The method of claim 21, further comprising:
    decoupling the retention device from the positioning block;
    repositioning the arm of the patient to a second desired position; and
    coupling the retention device to the positioning block to maintain the second desired position.

24. The method of claim 21, wherein the interface surface of the positioning block extends along a portion of the side surface of the positioning block in a substantially horizontal orientation.

25. The method of claim 21, wherein the desired position is a substantially palm-up position.

26. A system for positioning the arm of a patient for a diagnostic procedure comprising:
    a positioning block having an inclined upper surface configured to support a hand and elbow of a patient; and
    a restraint device configured to receive at least a portion of a hand of the patient, the restraint device having an attachment surface positioned thereon, wherein the positioning block comprises at least at least two elongated attachment surfaces located on a side surface of the positioning block and defining longitudinal axes, wherein the longitudinal axes of the two attachment surfaces are substantially parallel to one another and at least one of the two elongated attachment surfaces is configured to couple to the attachment surface on the restraint device to retain the hand of the patient in a substantially palm-up position with respect to the positioning block, and wherein the attachment surface on the positioning block is configured such that the restraint device can be repositioned to retain the arm in a second desired position with respect to the positioning block.

\* \* \* \* \*